United States Patent
Cheng et al.

(10) Patent No.: US 10,571,446 B2
(45) Date of Patent: Feb. 25, 2020

(54) DATA QUALITY CONTROL USING A CORRELATED SENSOR GROUP

(71) Applicant: International Business Machines Corporation, Armonk, NY (US)

(72) Inventors: Wen Chen Cheng, Beijing (CN); Xin Jie Lv, Beijing (CN); Xiao Guang Rui, Beijing (CN); Ling Yun Wang, Beijing (CN); Wen Jun Yin, Beijing (CN); Yu Ed Zhao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 268 days.

(21) Appl. No.: 15/498,762

(22) Filed: Apr. 27, 2017

(65) Prior Publication Data

US 2018/0313799 A1    Nov. 1, 2018

(51) Int. Cl.
*G01N 33/00* (2006.01)
*G01N 15/06* (2006.01)
*G01N 5/02* (2006.01)
*G01N 15/00* (2006.01)

(52) U.S. Cl.
CPC ............. *G01N 33/007* (2013.01); *G01N 5/02* (2013.01); *G01N 15/06* (2013.01); *G01N 15/0606* (2013.01); *G01N 15/0618* (2013.01); *G01N 2015/0046* (2013.01); *G01N 2015/0693* (2013.01)

(58) Field of Classification Search
CPC ........ G01N 33/007; G01N 15/06; G01N 5/02; G01N 15/0606; G01N 15/0618; G01N 2015/0693; G01N 2015/0046
See application file for complete search history.

(56) References Cited

U.S. PATENT DOCUMENTS

| | | | |
|---|---|---|---|
| 6,772,082 B2 * | 8/2004 | van der Geest | G01D 3/08 702/116 |
| 8,299,449 B2 | 10/2012 | Febo | |
| 9,952,189 B1 | 4/2018 | Chen et al. | |
| 10,082,787 B2 * | 9/2018 | Hara | G05B 23/0221 |

(Continued)

FOREIGN PATENT DOCUMENTS

| | | |
|---|---|---|
| CN | 201355339 | 12/2009 |
| CN | 104132863 | 11/2014 |

OTHER PUBLICATIONS

Thomann et al., "An efficient monitoring concept with control charts for on-line sensors", Water Science and Technology vol. 46 No. 4-5 pp. 107-116 2002 (Year: 2002).*

(Continued)

*Primary Examiner* — Regis J Betsch
(74) *Attorney, Agent, or Firm* — Fleit Intellectual Property Law; Jose Gutman (57) ABSTRACT

A system, a computer readable storage medium, and a method for data quality control using a correlated sensor group includes selecting a sensor group, by at least one processor, according to a uniformity and a correlation with air pollution concentration data from a reference station, selecting a time series based on the correlation, generating a particle concentration model between the sensor group and the reference station, calculating a deviation in the particle concentration data from the particle concentration model, and recognizing outliers from the deviation as unacceptable data.

20 Claims, 9 Drawing Sheets

(56) References Cited

U.S. PATENT DOCUMENTS

| | | | |
|---|---|---|---|
| 2006/0047482 A1* | 3/2006 | Yuan | G06F 11/0736 |
| | | | 702/185 |
| 2011/0313958 A1 | 12/2011 | Roverso | |
| 2015/0032266 A1 | 1/2015 | Weast et al. | |
| 2016/0142160 A1* | 5/2016 | Walker | H04W 4/70 |
| | | | 702/104 |
| 2018/0087954 A1* | 3/2018 | Gonzaga | G01F 25/0007 |
| 2018/0238789 A1* | 8/2018 | Ba | G01N 15/06 |
| 2019/0004023 A1 | 1/2019 | Kelly et al. | |

OTHER PUBLICATIONS

Larsen, et al., "Comparison of Particulate Monitoring Methods at Fort Air Partnership Monitoring Stations", Mar. 13, 2014, pp. 1-31.

Huang, C., "Field Comparison of Real-Time PM2.5 Readings from a Beta Gauge Monitor and a Light Scattering Method", Aerosol and Air Quality Research, Jun. 2007, pp. 1-12, vol. 7, No. 2.

Karagulian, F., et al., "Evaluation of a portable nephelometer against the Tapered Element Oscillating Microbalance method for monitoring PM2.5", Journal of Environmental Monitoring, Published on Jun. 13, 2012, vol. 14, No. 8, pp. 1-9.

Shrendrikar, A., et al., "Integrating nephelometer measurements for the airborne fine particulate matter (PM 2.5) mass concentrations", Atmospheric Environment, Mar. 2003, vol. 37, Issues 9-10, pp. 1383-1392.

* cited by examiner

Loss function: $R_{srm} = \frac{1}{T}\sum_{t=1}^{T} g(t)L(y_t, f(x_t)) + \gamma l(f)$ g(t) is time decay function

DATA QUALITY CONTROL USING A CORRELATED SENSOR GROUP

BACKGROUND

The present disclosure generally relates to a computer system and method, and more particularly relates to a system and method for data quality control using light scattering based sensors.

There are two general types of automated particle concentration monitoring stations or samplers that are widely used for particle concentration monitoring. The first of the two samplers uses a beta gauge for mass measurement and the second of the two samplers uses a tapered element oscillating microbalance (TEOM) for mass measurement. Beta gauge particulate samplers have an appearance that is similar to a reel to reel tape recorder. Air is pulled through a filter tape to accumulate a sample, the mass of the tape before and after sampling is determined by advancing the tape spot into the beta attenuation cell. The TEOM particulate sampler operates by drawing air through a filter attached at the tip of a glass tube. An electrical circuit places the tube into oscillation, and the resonant frequency of the tube is proportional to the square root of the mass on the filter. Both types of samplers suffer from poor data quality.

Existing methods to improve or verify the data suffer from poor efficiency or accuracy. A manual review of the data is very inefficient and could take quite a long time. Statistical methods can use simple thresholds, but suffer from poor accuracy.

SUMMARY

According to one embodiment of the present disclosure, a method for data quality control using a correlated sensor group includes (1) selecting a sensor group, by at least one or more processors of at least one computing device, according to a uniformity and a correlation with air pollution concentration data from a reference station, (2) selecting a time series based on the correlation, (3) generating a particle concentration model between the sensor group and the reference station, and (4) calculating, a deviation in the particle concentration data from the particle concentration model, by the at least one or more processors. The method can further include recognizing outliers from the deviation as unacceptable data.

According to another embodiment of the present disclosure, a system for data quality control using a correlated sensor group includes at least one processor of a computer system communicatively coupled to at least one memory. Responsive to instructions stored in memory, the processor(s) can perform a method that includes the following operations: (1) selecting a sensor group, by the at least one processor, according to a uniformity and a correlation with air pollution concentration data from a reference station, (2) selecting a time series based on the correlation, (3) generating a particle concentration model between the sensor group and the reference station, (4) calculating a deviation in the particle concentration data from the particle concentration model, and (5) recognizing, by the at least one processor, outliers from the deviation as unacceptable data.

According to yet another embodiment of the present disclosure, a non-transitory computer readable storage medium can include computer instructions which, responsive to being executed by one or more processors, cause the processor(s) to perform operations as described in the methods or systems above or elsewhere herein.

BRIEF DESCRIPTION OF THE DRAWINGS

The accompanying figures, in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

As required, detailed embodiments of the present disclosure are disclosed herein; however, it is to be understood that the disclosed embodiments are merely examples of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure and function. Further, the terms and phrases used herein are not intended to be limiting; but rather, to provide an understandable description of the disclosure.

According to various embodiments of the present disclosure, disclosed is a system and method for data quality control using a correlated sensor group such as an inexpensive light scattering sensor paired in a group of two or more sensors to enhance results from existing particle monitoring systems. The embodiments utilize the discovery of a dynamic linear or quadratic relationship that exists between the light scattering sensor and the standard particle concentration sensors (e.g., TEOM, or beta gauge or beta ray type sensor stations) in short time series. Thus, in some embodiments, a simple model can be dynamically built between the light scatter method and the standard particle concentration monitoring stations to readily recognize unacceptable data through deviation outliers in a selected time series.

Figure 1:
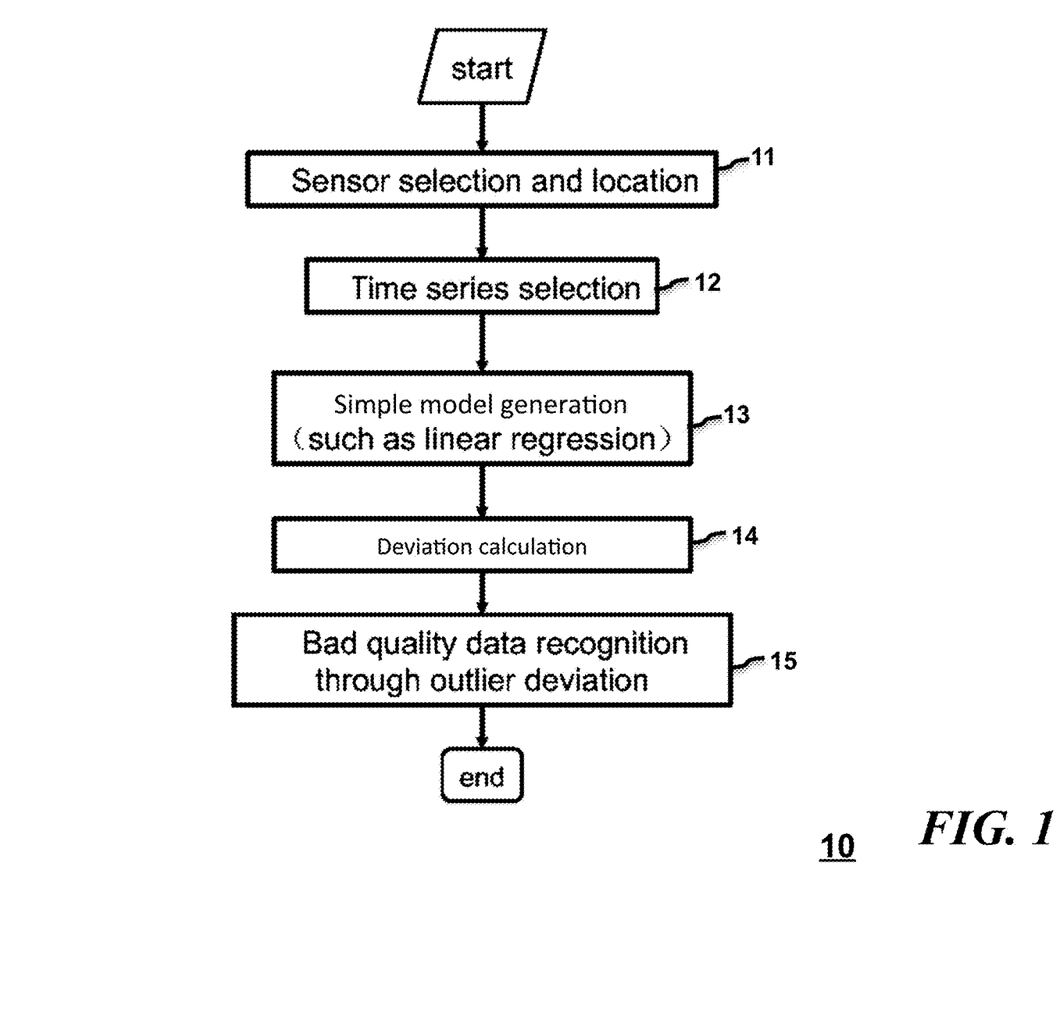
FIG. 1 is a depiction of flow diagram of a system or method for data quality control using a correlated sensor group according to various embodiments of the present disclosure.

More specifically, referring to a method 10 of FIG. 1, a sensor group that can be made of at least a pair of light scattering sensors can be selected at block 11 in accordance with their uniformity (between the sensors of the pair) and correlation with the reference station. The sensor groups can also be located at block 11 in the same place with each standard station and a dynamic time series is selected at block 12 based on the correlation. The method and system can then generate at block 13 a particle concentration model between the sensor group and the standard station, for instance, using a linear regression formula or model. The system and method can calculate a deviation at block 14 and recognize unacceptable data through deviation outliers at block 15.

Figure 2:
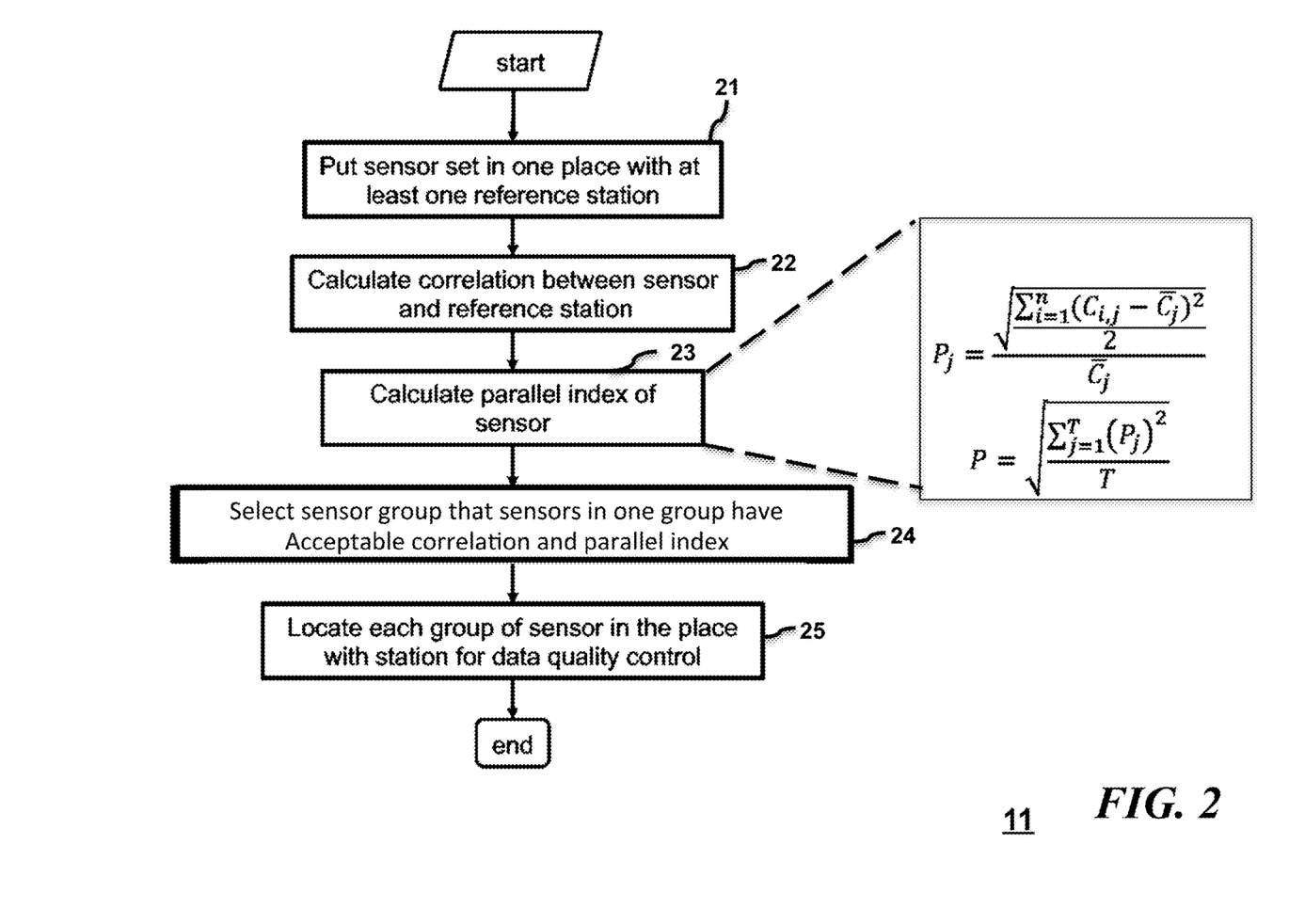
FIG. 2 is a depiction of flow diagram of a portion of the system or method for data quality control using a correlated sensor group that performs sensor selection and location according to various embodiments of the present disclosure.

FIGS. 2-9 provide further details of the individual blocks of the method 10. For example, FIG. 2 illustrates a flow chart of the sensor selection and location block 11 that includes putting a sensor set or sensor group in one place or location with at least one reference station at block 21. In practice, the sensor group can be co-located with the reference station or integrated with the reference station. In some embodiments, the sensor group can be placed directly adjacent to the reference station. At block 22, the method 11 calculates a correlation between the sensor (or sensor group) and the reference station. At block 23, the method 11 can calculate a parallel index of the sensor, using the following formulas as example:

$$P_j = \frac{\sqrt{\frac{\sum_{i=1}^{n}(C_{i,j} - \overline{C}_j)^2}{2}}}{\overline{C}_j}$$

$$P = \sqrt{\frac{\sum_{j=1}^{T}(P_j)^2}{T}}$$

where
$P_j$—the jth sample's relative deviation of the sensor group, %
$C_{i,j}$—the jth sample's PM25 concentration of the ith sensor, ug/m3
$\overline{C}_j$—average of the jth sample's PM25 concentration of the sensor group, ug/m3
P—the parallel index of the sensor group, %

At block 24, a sensor group is selected where at least a sensor in one group has an acceptable correlation level and an acceptable parallel index. The method 11 can then locate each group of sensors in the location with the station to maintain data quality control at block 25. The reason for using more than one sensor in a sensor group and using a sensor group as part of the process is to eliminate exceptions or outliers among the sensor groups. Thus, only those sensors groups that have very similar outputs among individual sensors are generally used.

Figure 3:
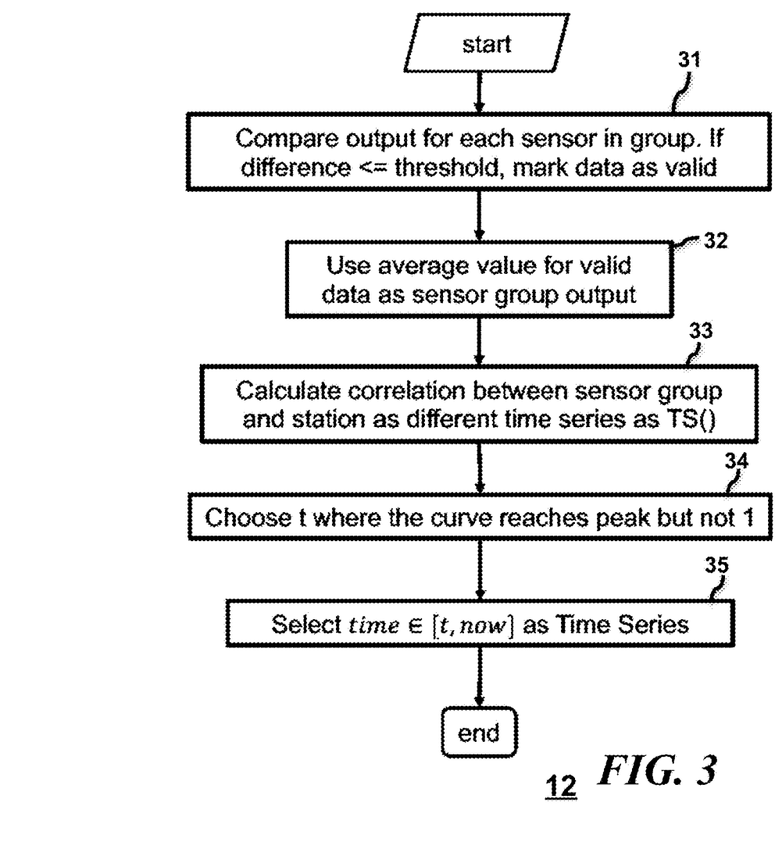
FIG. 3 is depiction of flow diagram of a portion of the system or method for data quality control using a correlated sensor group that performs time series selection according to various embodiments of the present disclosure.
Figure 4:
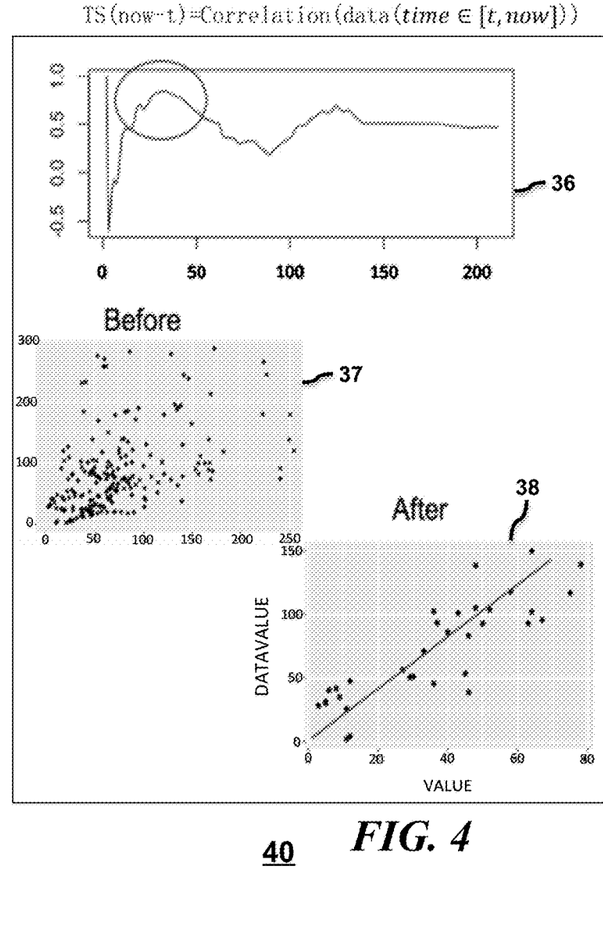
FIG. 4 is a depiction of a time series curve and corresponding before and after scatter plots according to various embodiments of the present disclosure.

Light scattering method sensors are much less costly or inexpensive than "standard particle monitoring stations" (also referred to herein as "station" or "stations") and generally have great differences in accuracies reflected by the cost. However, in a short time series, the trend of both the cheaper light scattering method sensor and the standard particle monitoring stations are consistent. Therefore, by selecting the appropriate kind of the time series, a set of outputs from the standard stations and the light scattering sensors can provide a consistent trend and a means for extracting poor data from quality data. FIG. 3 illustrates a more detailed flow chart of the time series selection block 12 of FIG. 1, which includes comparing the output for each sensor in a group and marking data as valid if the difference between the outputs are equal to or less than a threshold at block 31. The method further includes using an average value for the valid data as the sensor group output at block 32 and calculating a correlation between the sensor group and station as a different time series as TS( ) at block 33. At block 34, t is chosen so that the curve of the time series reaches a peak, but not one (1). In the set 40 of FIG. 4, the chart 36 represents the curve where t is at its peak, but not one. At block 35 of FIG. 3, selection of time∈[t, now] as a Time Series. In other words, once the outputs from the sensor group and station are obtained, the correlation coefficients can be calculated as $TS(\text{now}-t)=\text{Correlation}(\text{data}(\text{time}\in[t,\text{now}]))$ In the set 40 of FIG. 4, a scatter plot of the data is shown before the time series selection in chart 37 and a scatter plot of the data after the time series selection is shown in chart 38.

Figure 5:
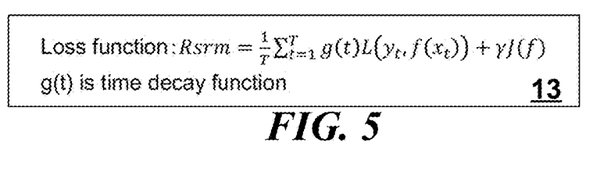
FIG. 5 is a simple model example using a linear regression formula according to various embodiments of the present disclosure.

FIG. 5 illustrates a more detailed representation of a simple model of block 13 of FIG. 1 that includes a particular linear regression formula or Loss function:

$$\text{Loss function: } Rsrm = \frac{1}{T}\sum_{t=1}^{T}g(t)L(y_t, f(x_t)) + \gamma j(f)$$

$g(t)$ is time decay function

Regarding the formula above, t is time, $x_t$ is output of Sensor group at time t, $y_t$ is the output of Station at time t. Then Rsrm is minimized to get the model f. If the output of Sensor group is used as $x_t$, then the calculation of yyt=f($x_t$). When comparing yyt and yt, the residuals is the absolute value of (yt−yyt). As noted further below, the definition of deviation1=residuals/f(xt) and the definition of deviation2=residuals. So we get two different kinds of deviation.

Figure 6:
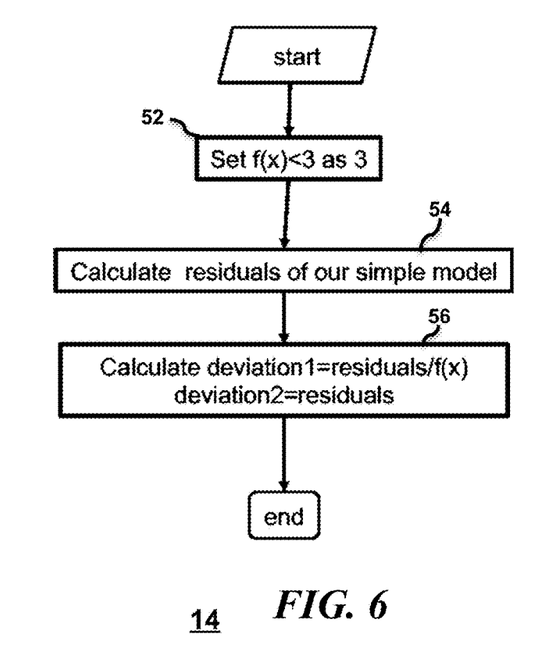
FIG. 6 is a flow diagram illustrating a portion of the system or method for data quality control using a correlated sensor group that performs the function of calculating a deviation according to various embodiments of the present disclosure.
Figure 7:
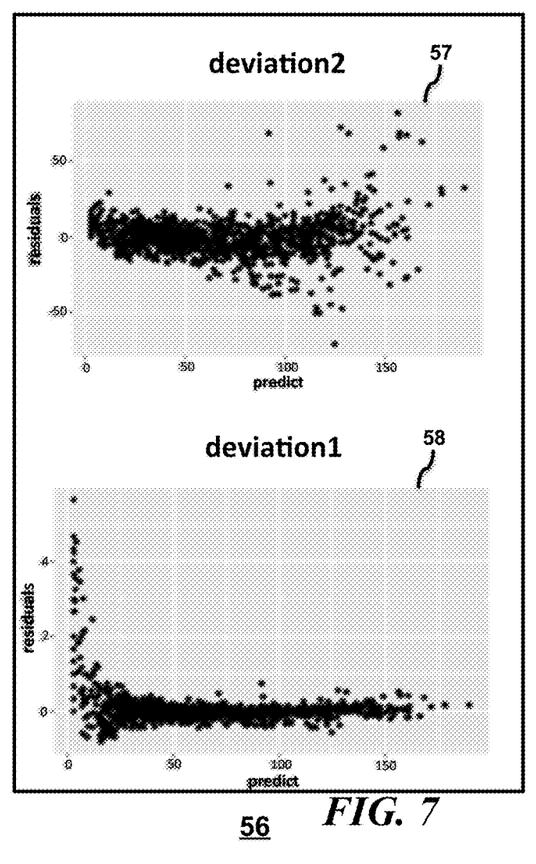
FIG. 7 is a depiction of scatter plots for a first deviation and a second deviation according to various embodiments of the present disclosure.

FIG. 6 illustrates a more detailed flow chart of the deviation calculation block 14 of FIG. 1 that includes setting f(x)<3 as 3 at block 52 and then calculating the residuals of the simple model at block 54. Two deviations are calculated at block 56 where deviation1=residuals/f(x) as represented by chart 58 of the set 56 of FIG. 7 and deviation2=residuals as represented by chart 57 of the set 56 of FIG. 7.

Figure 8:
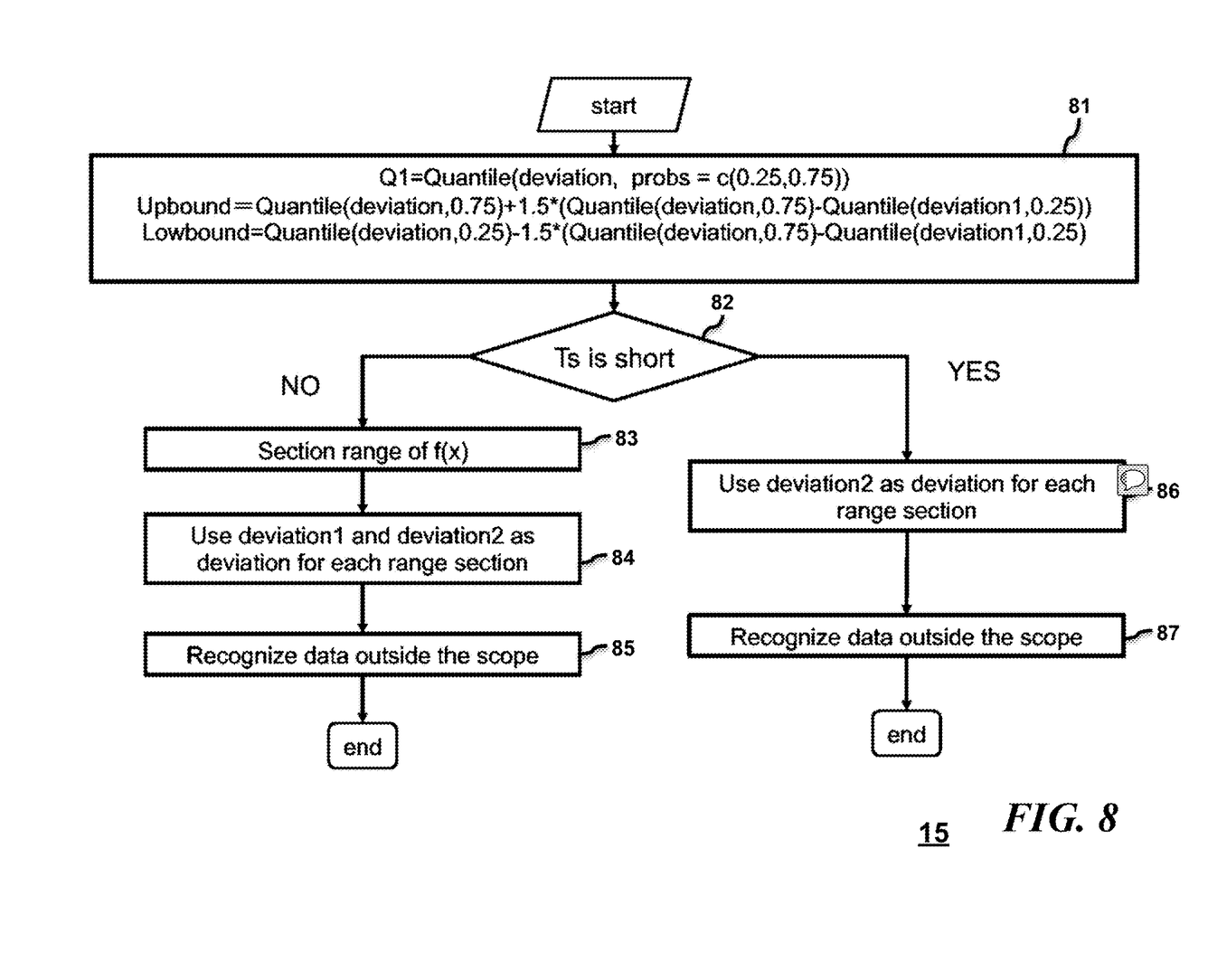
FIG. 8 is a flow diagram illustrating a portion of the system or method for data quality control using a correlated sensor group that performs the function of bad quality data recognition through outlier deviation according to various embodiments of the present disclosure.
Figure 9:
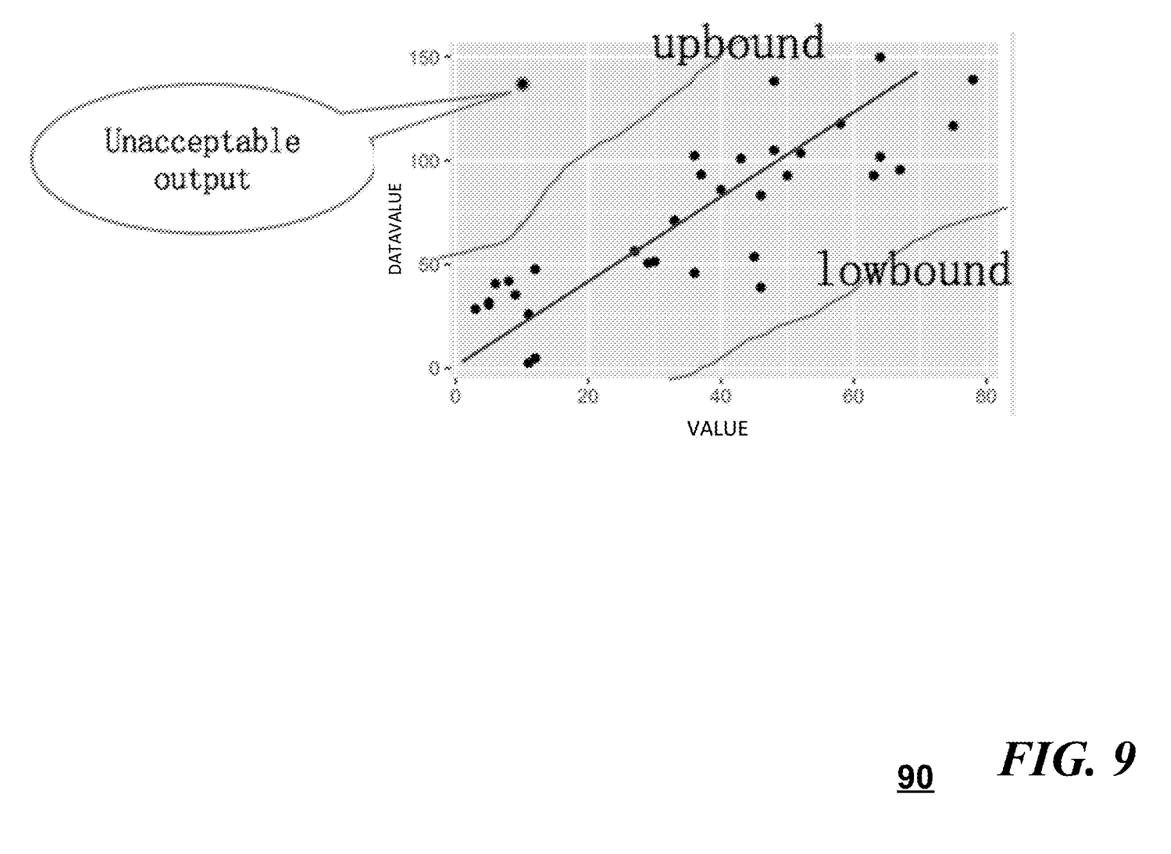
FIG. 9 is a depiction of a scatter plot showing upper and lower boundaries used to identify outlier deviations according to various embodiments of the present disclosure.

FIG. 8 illustrates a more detailed flow chart of the bad quality data recognition through outlier deviation method of block 15 of FIG. 1. This step generates an acceptable deviation interval where an upper bound and a lower bound as reflected in the chart 90 of FIG. 9 are used to calculate the interval. If the deviation is outside the interval, then the output outside the interval is considered unacceptable. At block 81, quantiles are used to determine the upper bound and lower bound as shown. If the Time Series Ts is not too short at decision block 82, then the method 15 sections the range of f(x) at block 83 and the deviation1 and deviation2 are used as the deviation for each range section at block 84. Then the method 15 recognizes the data outside the scope at block 85. If the Time Series Ts is too short at decision block 82, then deviation2 is used as the deviation for each range section at block 86 and then the method 15 recognized the data outside the scope at block 87.

In one example, the section of the range of f(x)=yyt. Since different levels of outputs may have different kinds of interval, the method can calculate intervals by different range.

For example, when yyt>0 and yyt<35, the upper bound of deviation may be 20 and lower bound of deviation maybe −15. If Yyt>200 and yyt<250, the upper bound of deviation may be 30 and lower bound of deviation maybe −30. If the interval for different ranges are not calculated, an unacceptable output during 0 and 35 may be missed.

Figure 10:
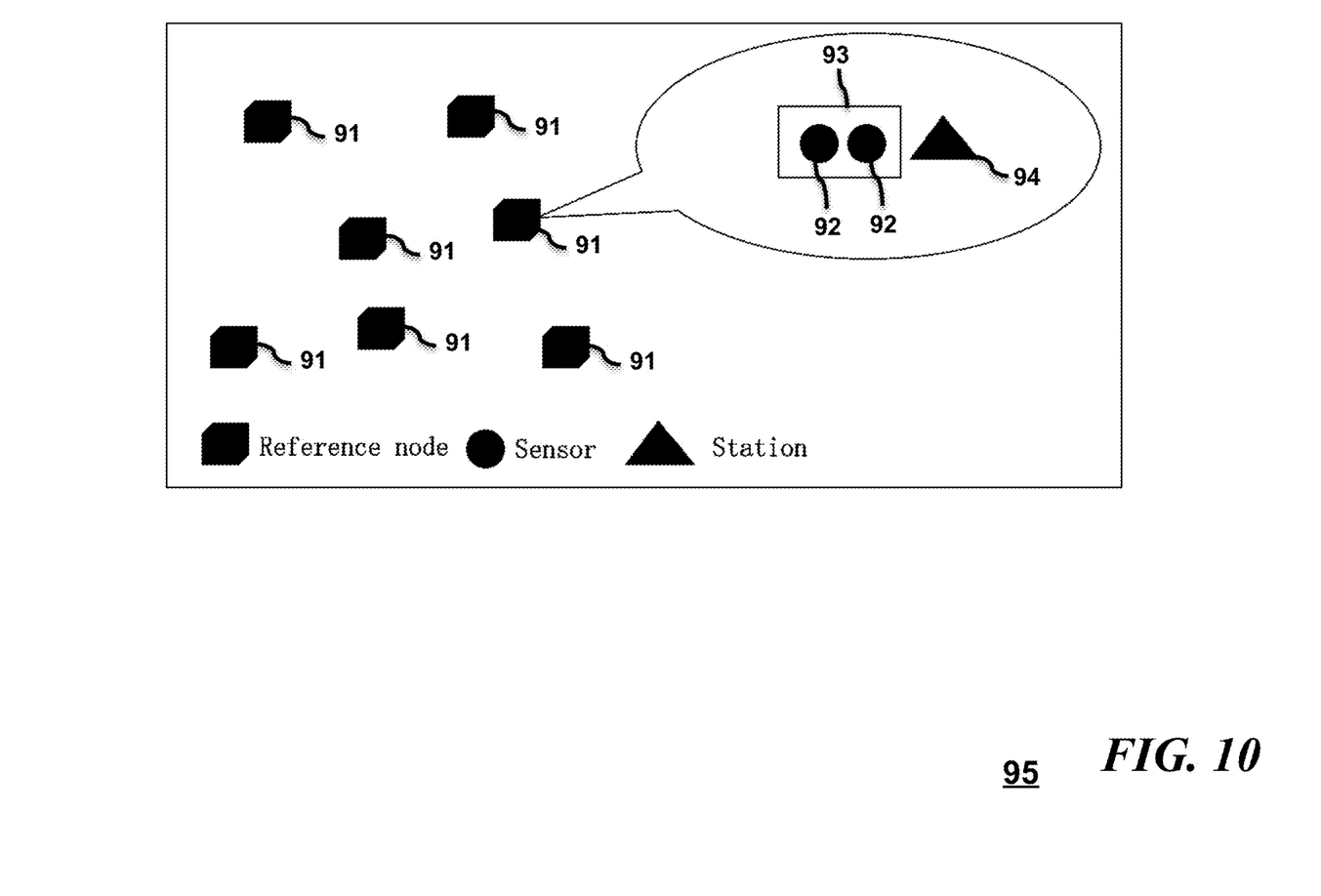
FIG. 10 is a block diagram of a system illustrating reference nodes, sensors, sensor groups, and a station associated with a sensor group to make up a reference node according to various embodiments of the present disclosure.

A system 95 of FIG. 10 illustrates a particular environment populated by reference nodes 91. Each reference node 91 or at least reference nodes in accordance with some of the embodiments would include a station 94 (also known as a "standard particle monitoring station") and a sensor group 93 that can include at least two sensors 92 such as two light scattering sensors.

In some embodiments, a system includes at least one memory and at least one processor of a computer system communicatively coupled to the at least one memory. The at least one processor can be configured to perform a method including methods described above.

According yet to another embodiment of the present disclosure, a computer readable storage medium comprises computer instructions which, responsive to being executed by one or more processors, cause the one or more processors to perform operations as described in the methods or systems above or elsewhere herein.

Figure 11:
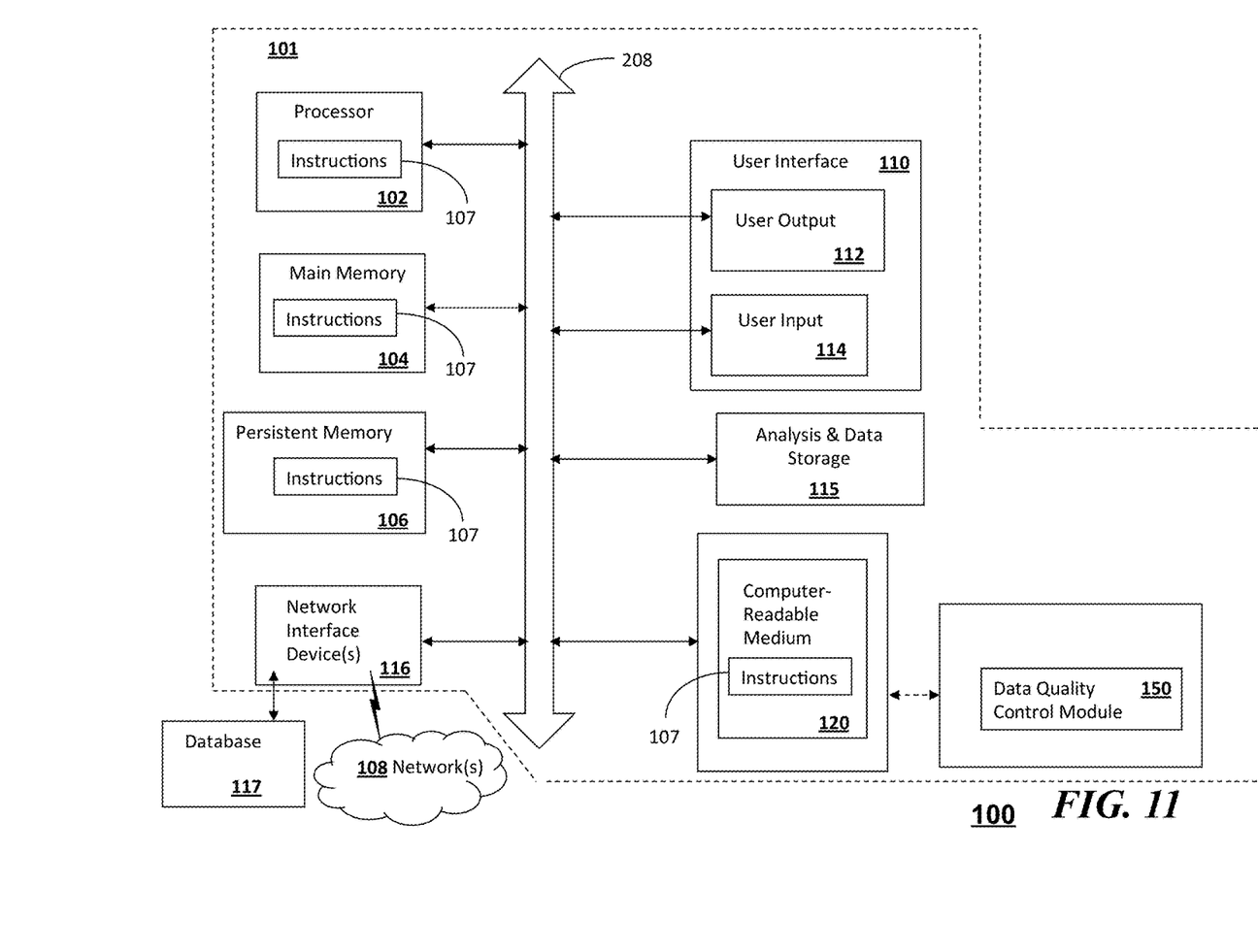
FIG. 11 is a block diagram of a system according to various embodiment of the present disclosure.

As shown in FIG. 11, an information processing system 101 of a system 100 can be communicatively coupled with the data quality control module 150 and a group of client or other devices, or coupled to a presentation device for display at any location at a terminal or server location. According to this example, at least one processor 102, responsive to executing instructions 107, performs operations to communicate with the data quality control module 150 via a bus architecture 208, as shown. The at least one processor 102 is communicatively coupled with main memory 104, persistent memory 106, and a computer readable medium 120. The processor 102 is communicatively coupled with an Analysis & Data Storage 115 that, according to various implementations, can maintain stored information used by, for example, the data quality control module 150 and more generally used by the information processing system 100. Optionally, this stored information can be received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The data quality control module 150, and the information processing system 100, can use the information from the history log such as in the analysis process and in making decisions related to determining whether data measured is considered an outlier or not.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

The information processing system 100 includes a user interface 110 that comprises a user output interface 112 and user input interface 114. Examples of elements of the user output interface 112 can include a display, a speaker, one or more indicator lights, one or more transducers that generate audible indicators, and a haptic signal generator. Examples of elements of the user input interface 114 can include a keyboard, a keypad, a mouse, a track pad, a touch pad, a microphone that receives audio signals, a camera, a video camera, or a scanner that scans images. The received audio signals or scanned images, for example, can be converted to electronic digital representation and stored in memory, and optionally can be used with corresponding voice or image recognition software executed by the processor 102 to receive user input data and commands, or to receive test data for example.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can intercommunicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present disclosure. The network interface device 116 can provide a communication interface for the information processing system 100 to access the at least one database 117 according to various embodiments of the disclosure.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

Figure 12:
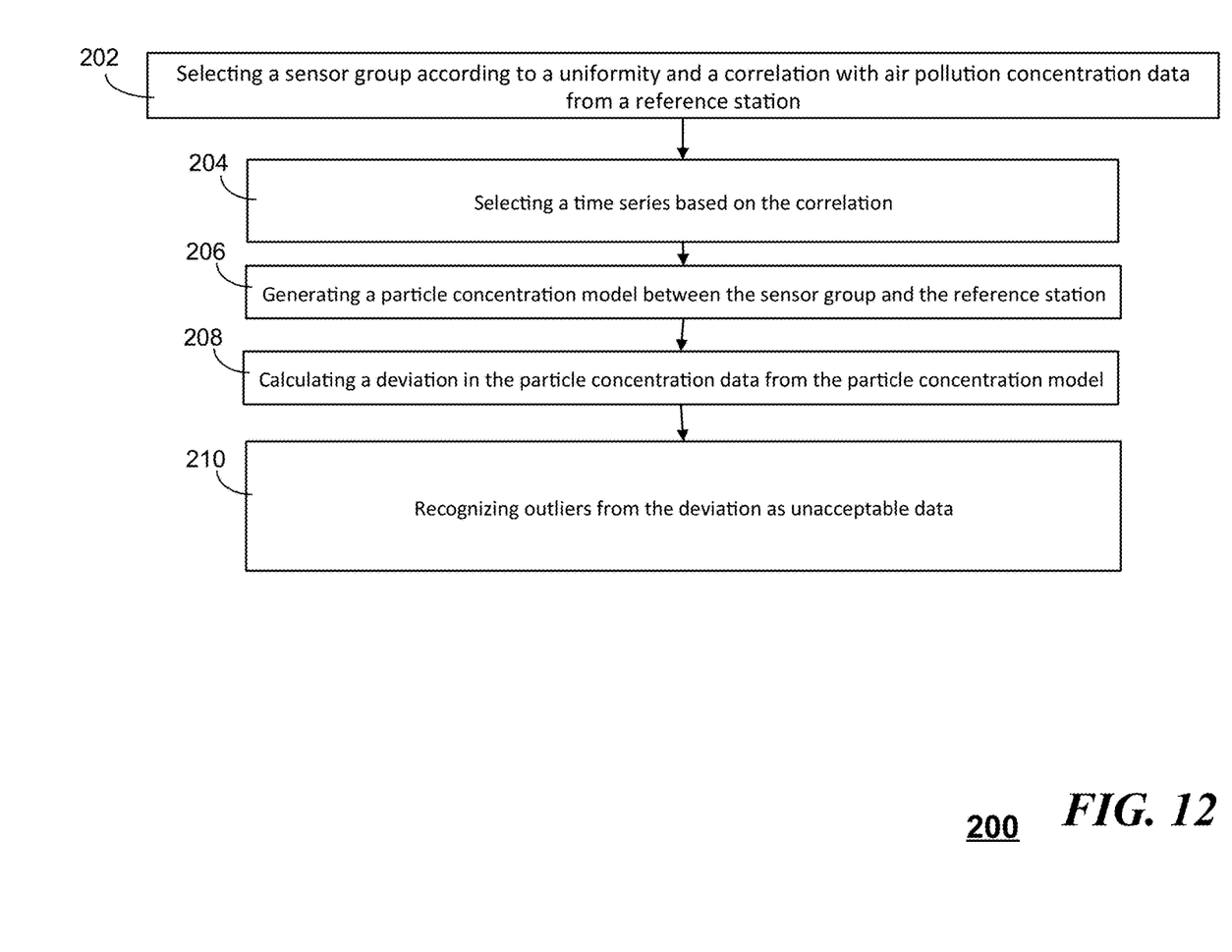
FIG. 12 is another depiction of flow diagram of a method for data quality control using a correlated sensor group according to various embodiments of the present disclosure.

FIG. 12 illustrates an example of a method, according to various embodiments of the present disclosure, which can operate in conjunction with the information processing system of FIG. 10. Specifically, according to the example shown in FIG. 12, a method 200 for data quality control can include at 202 of selecting a sensor group according to uniformity between the sensors of the sensor group and according to a correlation with air pollution concentration data from a reference station or standard station. The method can further include selecting a time series based on the correlation at 204 and generating a model between the sensor group and the reference station at 206. At 208, the method 200 can calculate a deviation in the particle concentration data from the particle concentration data from the model. With the deviation (or deviations), the method 200 can recognize the outliers in the particle concentration data and set them (or discard them) as unacceptable data at 210.

Non-Limiting Examples

The examples provide herein may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present specification may describe components and functions implemented in the embodiments with reference to particular standards and protocols, the disclosure is not limited to such standards and protocols. Each of the standards represents examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single example embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Although only one processor is illustrated for an information processing system, information processing systems with multiple CPUs or processors can be used equally effectively. Various embodiments of the present disclosure can further incorporate interfaces that each includes separate, fully programmed microprocessors that are used to off-load processing from the processor. An operating system (not shown) included in main memory for the information processing system may be a suitable multitasking and/or multiprocessing operating system, such as, but not limited to, any of the Linux, UNIX, Windows, and Windows Server based operating systems. Various embodiments of the present disclosure are able to use any other suitable operating system. Various embodiments of the present disclosure utilize architectures, such as an object oriented framework mechanism, that allows instructions of the components of operating system (not shown) to be executed on any processor located within the information processing system. Various embodiments of the present disclosure are able to be adapted to work with any data communications connections including present day analog and/or digital techniques or via a future networking mechanism.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The terms "communicatively coupled" or "communicatively coupling" include, but are not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer system", "computing system", "personal computing system", "processing system", or "information processing system", describe examples of a suitably configured processing system adapted to implement one or more embodiments herein. Any suitably configured processing system is similarly able to be used by embodiments herein, for example and not for limitation, a personal computer, a laptop personal computer (laptop PC), a tablet computer, a smart phone, a mobile phone, a wireless communication device, a personal digital assistant, a workstation, and the like. A processing system may include one or more processing systems or processors. A processing system can be realized in a centralized fashion in one processing system or in a distributed fashion where different elements are spread across several interconnected processing systems.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. A computer implemented method, comprising:
   selecting a sensor group, by at least one or more processors of at least one computing device, according to a uniformity and a correlation with air pollution concentration data from a reference station;
   selecting, by the at least one or more processors, a time series based on the correlation;
   generating, by the at least one or more processors, a particle concentration model between the sensor group and the reference station;
   calculating, by the at least one or more processors, a deviation in the particle concentration data from the particle concentration model; and
   recognizing, by the at least one or more processors, outliers from the deviation as unacceptable data.

2. The computer implemented method of claim 1, wherein the sensor group is co-located with the reference station.

3. The computer implemented method of claim 1, wherein the sensor group is at least a pair of light scattering sensors co-located with the reference station.

4. The computer implemented method of claim 1, wherein the selecting of the sensor group comprises:
   placing the sensor group with at least the reference station;
   calculating a parallel index of a sensor among a plurality of sensor groups; and
   selecting the sensor group having an acceptable correlation and an acceptable parallel index.

5. The computer implemented method of claim 1, wherein the selecting of the time series comprises:
   comparing an output for each sensor in the sensor group with a difference threshold and designating the output for each sensor as a valid output if the output is less than or equal to the difference threshold;
   using an average value of the valid outputs between each sensor in the sensor group;
   calculating a correlation between the sensor group output and the reference station output as different time series; and
   select a time series among the different time series where a curve for the correlation reaches a peak not equal to one.

6. The computer implemented method of claim 1, wherein generating the particle concentration model between the sensor group and the reference station comprises using linear regression.

7. The computer implemented method of claim 1, wherein generating the particle concentration model between the sensor group and the reference station comprises using as inputs sensor group outputs for particle number, particle concentration, and humidity, and using as targets a reference station particle concentration.

8. The computer implemented method of claim 1, wherein generating the particle concentration model between the sensor group and the reference station comprises using linear regression by using a loss function of $Rsrm = 1/T\Sigma_{t=1}^{T} g(t)L(y_t, f(x_t)) + \gamma J(f)$ where $g(t)$ is a time decay function.

9. The computer implemented method of claim 1, wherein the calculating of the deviation in the particle concentration data from the particle concentration model comprises calculating residuals from the particle concentration model.

10. The computer implemented method of claim 1, wherein the calculating of the deviation in the particle concentration data from the particle concentration model comprises calculating a first deviation and a second deviation using residuals from the particle concentration model.

11. A system comprising:
    at least one memory; and
    at least one processor of a computer system communicatively coupled to the at least one memory, the at least one processor, responsive to instructions stored in memory, being configured to perform a method comprising:
    selecting a sensor group, by the at least one processor, according to a uniformity and a correlation with air pollution concentration data from a reference station;
    selecting, by the at least one processor, a time series based on the correlation;
    generating, by the at least one processor, a particle concentration model between the sensor group and the reference station;
    calculating, by the at least one processor, a deviation in the particle concentration data from the particle concentration model; and
    recognizing, by the at least one processor, outliers from the deviation as unacceptable data.

12. The system of claim 11, wherein the sensor group are integrated and co-located with the reference station.

13. The system of claim 11, wherein the sensor group comprises at least a pair of light scattering sensors co-located with the reference station.

14. The system of claim 11, wherein the selecting of the sensor group comprises:
    placing the sensor group with at least the reference station;
    calculating a parallel index of a sensor among a plurality of sensor groups; and
    selecting the sensor group having an acceptable correlation and an acceptable parallel index.

15. The system of claim 11, wherein the selecting of the time series comprises:
    comparing an output for each sensor in the sensor group with a difference threshold and designating the output for each sensor as a valid output if the output is less than or equal to the difference threshold;
    using an average value of the valid outputs between each sensor in the sensor group;
    calculating a correlation between the sensor group output and the reference station output as different time series; and
    select a time series among the different time series where a curve for the correlation reaches a peak not equal to one.

16. The system of claim 11, wherein generating the particle concentration model between the sensor group and the reference station comprises using linear regression.

17. The system of claim 11, wherein generating the particle concentration model between the sensor group and the reference station comprises using as inputs sensor group outputs for particle number, particle concentration, and humidity, and using as targets a reference station particle concentration.

18. The system of claim 11, wherein the sensor group comprises at least a pair of light scattering sensors integrated with the reference station and wherein the reference station uses a beta gauge for mass measurement or a tapered element oscillating microbalance for mass measurement.

19. The system of claim 11, wherein the at least one processor performs the functions of sensor group selector, sensor group locator, dynamic time series selector, model builder, deviation calculator, and unacceptable data recognizer.

20. A non-transitory computer-readable storage medium having stored therein instructions which, when executed by at least one or more processors of at least one computing device, cause a computer system to perform a method comprising:
- selecting a sensor group, by the at least one or more processors, according to a uniformity and a correlation with air pollution concentration data from a reference station;
- selecting, by the at least one or more processors, a time series based on the correlation;
- generating, by the at least one or more processors, a particle concentration model between the sensor group and the reference station;
- calculating, by the at least one or more processors, a deviation in the particle concentration data from the particle concentration model; and
- recognizing, by the at least one or more processors, outliers from the deviation as unacceptable data.

* * * * *